(12) United States Patent
Ehrlinspiel et al.

(10) Patent No.: US 8,858,616 B2
(45) Date of Patent: Oct. 14, 2014

(54) STENT HAVING A BRIDGE STRUCTURE

(75) Inventors: Michael Ehrlinspiel, Weingarten (DE); Erik Flaxmeier, Karlsbad (DE); Alexander Lange, Karlsruhe (DE)

(73) Assignee: Admedes Schuessler GmbH, Pforzheim (DE)

( * ) Notice: Subject to any disclaimer, the term of this patent is extended or adjusted under 35 U.S.C. 154(b) by 201 days.

(21) Appl. No.: 13/022,475

(22) Filed: Feb. 7, 2011

(65) Prior Publication Data

US 2011/0251673 A1 Oct. 13, 2011

Related U.S. Application Data

(63) Continuation-in-part of application No. 11/081,852, filed on Mar. 16, 2005, now abandoned.

(30) Foreign Application Priority Data

Mar. 16, 2004 (DE) .......................... 10 2004 012 837

(51) Int. Cl.
*A61F 2/86* (2013.01)
*A61F 2/915* (2013.01)
*A61F 2/91* (2013.01)

(52) U.S. Cl.
CPC ....... *A61F 2/915* (2013.01); *A61F 2002/91533* (2013.01); *A61F 2/91* (2013.01)
USPC ...................................................... 623/1.15

(58) Field of Classification Search
CPC ............... A61F 2/89; A61F 2/90; A61F 2/91; A61F 2/915
USPC ................... 606/194, 200; 623/1.15, 1.16
See application file for complete search history.

(56) References Cited

U.S. PATENT DOCUMENTS

| 5,681,280 A | 10/1997 | Rusk et al. |
| 5,725,525 A | 3/1998 | Kordis |
| 5,730,128 A | 3/1998 | Pomeranz et al. |
| 5,922,021 A * | 7/1999 | Jang .............................. 623/1.15 |
| 6,019,789 A * | 2/2000 | Dinh et al. .................... 623/1.15 |
| 6,039,756 A | 3/2000 | Jang |
| 6,132,461 A | 10/2000 | Thompson |
| 6,245,101 B1 | 6/2001 | Drasler et al. |

(Continued)

FOREIGN PATENT DOCUMENTS

| DE | 19653721 | 4/1998 |
| DE | 202004000896 | 4/2004 |

(Continued)

OTHER PUBLICATIONS

European Search Report, Admedes Schuessler GmgH, May 5, 2004.

(Continued)

*Primary Examiner* — Kathleen Holwerda
(74) *Attorney, Agent, or Firm* — McDonald Hopkins LLC

(57) ABSTRACT

In a stent intended for implantation in a living body and having a bridge structure in which at least two bridges are coupled to one another at at least one node region on at least one of the bridges near the node region, the section modulus of the bridge varies along the length thereof, and the stresses arising at the node region upon deformation of the stent are distributed in the longitudinal direction of the bridge.

7 Claims, 4 Drawing Sheets

(56) References Cited

U.S. PATENT DOCUMENTS

| | | |
|---|---|---|
| 6,319,251 B1 | 11/2001 | Tu et al. |
| 6,391,044 B1 | 5/2002 | Yadav et al. |
| 6,416,543 B1 | 7/2002 | Hilaire et al. |
| 6,520,985 B1 | 2/2003 | Burpee et al. |
| 6,626,935 B1 | 9/2003 | Ainsworth et al. |
| 6,699,278 B2 | 3/2004 | Fischell et al. |
| 6,758,859 B1 * | 7/2004 | Dang et al. ............... 623/1.15 |
| 6,863,685 B2 | 3/2005 | Davila et al. |
| 6,896,698 B2 * | 5/2005 | Rolando et al. ............ 623/1.16 |
| 7,014,654 B2 * | 3/2006 | Welsh et al. ............... 623/1.15 |
| 7,029,492 B1 * | 4/2006 | Mitsudou et al. .......... 623/1.15 |
| 2001/0027339 A1 | 10/2001 | Boatman et al. |
| 2001/0029660 A1 | 10/2001 | Johnson |
| 2002/0016623 A1 | 2/2002 | Kula et al. |
| 2002/0103501 A1 | 8/2002 | Diaz et al. |
| 2002/0111671 A1 | 8/2002 | Stenzel |
| 2002/0198593 A1 | 12/2002 | Gomez et al. |
| 2003/0014102 A1 * | 1/2003 | Hong et al. ................ 623/1.15 |
| 2003/0105511 A1 * | 6/2003 | Welsh et al. ............... 623/1.15 |
| 2003/0176914 A1 * | 9/2003 | Rabkin et al. .............. 623/1.15 |
| 2003/0199969 A1 | 10/2003 | Steinke et al. |
| 2004/0153056 A1 | 8/2004 | Muller et al. |
| 2005/0015138 A1 | 1/2005 | Schuessler et al. |
| 2007/0067017 A1 * | 3/2007 | Trapp ........................ 623/1.16 |

FOREIGN PATENT DOCUMENTS

| | | |
|---|---|---|
| EP | 1042997 | 10/2000 |
| EP | 1190685 | 3/2002 |
| EP | 1236448 | 9/2002 |
| EP | 1356789 | 10/2003 |
| WO | WO97/26840 | 7/1997 |
| WO | WO01/15632 | 3/2001 |
| WO | WO01/58382 | 8/2001 |
| WO | WO2004/043279 | 5/2004 |

OTHER PUBLICATIONS

European Search Report, Admedes Schuessler GmgH, May 10, 2005.

* cited by examiner

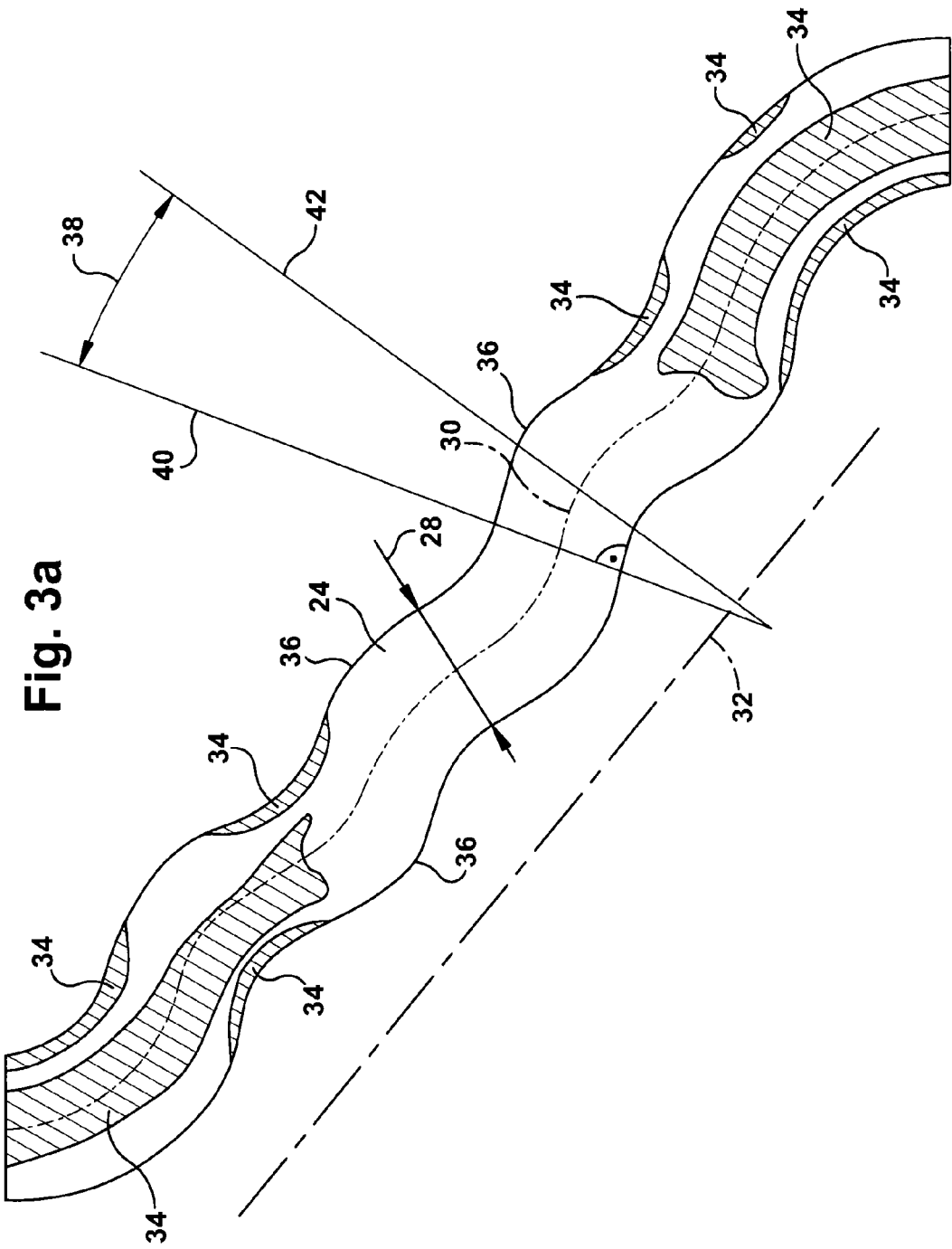

STENT HAVING A BRIDGE STRUCTURE

CROSS-REFERENCE TO RELATED APPLICATIONS

This application is a continuation-in-part of U.S. patent application Ser. No. 11/081,852 which is now abandoned and was filed on Mar. 16, 2005, and which claims priority from German Patent Application No. 10 2004 012 837.5-43 filed on Mar. 16, 2004, each of which is hereby incorporated by reference.

FIELD OF INVENTION

The present invention relates generally to stents intended for implantation in a living body, and in particular, to an intraluminal stent, and having a bridge structure in which at least two bridges are coupled to one another at least one node region. The present invention also relates generally to a method for producing such a stent.

BACKGROUND

Stents of this kind are used to protect against collapse or occlusion of channels in living bodies, for example blood vessels, esophagus, urethra or renal ducts, by expansion of their tubular bridge structure inside the channel. They also serve as carriers for medicaments in channels of the body and thus permit local therapy inside the channel.

The bridge structure of such stents is composed of a large number of bridges that are in each case connected to one another at node regions and delimit individual cells arranged alongside one another. By widening of the individual cells, the bridge structure as a whole can be expanded, and in some stents, can also be reduced in size again by making the cells smaller. The bridges thus form connection elements between the node regions that are substantially stiff and make a large contribution to the supporting action of a stent.

To ensure that the stent bears on the channel wall, it has to be able to expand radially in the channel. Additionally, in the expanded state, the stent must be able to fulfill its support function. The aim, therefore, is to design a stent optimally in terms of its deformation behavior and in terms of the resulting elongation and stress.

SUMMARY OF THE INVENTION

An object of the invention is to make available a stent having a bridge structure that permits the greatest possible diameter ratio between the expanded state and the compressed state. In this way it should be possible to provide access into very small vessels and also ensure support of very large vessels.

According to the invention, the object is achieved with a stent in which at at least one of the bridges near the node region, the section modulus of the bridge varies along the length thereof, and the stresses arising at the node region upon deformation of the stent are distributed in the longitudinal direction of the bridge. According to the invention, the object is also achieved by a method as claimed in claim 5. Advantageous developments of a stent according to the invention and of the method are set out in the dependent claims.

In known stents, although it is likewise possible in principle to select a relatively large ratio of size between the nonexpanded state and the expanded state, the stents, however, increasingly lose their supporting force, or so-called radial force, in the expanded state. The radial force is, however, an important attribute for the use of stents.

The invention is based on the knowledge that with an increasing ratio of the size of stents, greater deformations of the bridge structure also occurs. This in turn induces greater stress in the material used. If the stresses exceed given material limits, which can generally be elongation at break and stress at break, this leads to damage of the respective element within the bridge structure of the stent. In addition, the deformed element is subject, during use, to an alternating permanent load, which, if the maximum specific to the material is exceeded, causes premature fatigue of the structural part.

To avoid this in the stent according to the invention, the induced stresses are relatively low, even at a relatively high deformation rate. Additionally, the strength of the bridge structure is comparatively great after the deformation, for example after an expansion. This bridge structure according to the invention can therefore withstand a relatively large number of alternate deformations.

According to the invention, the maximum stresses occurring are reduced by the stresses being distributed uniformly into the bridge structure of the stent. The deformation energy is thus shifted from the regions of greatest load to regions of less load.

FIG. 1 shows a section of a bridge structure 10 of a known stent 12, in which bridges 14 are provided near the node regions 16 with tapers 18 for distributing stresses within the bridge structure 10. The tapers 18 are intended to shift deformation energy from the regions of greatest load to regions where there is less load. Since the structure at the tapers takes up more deformation energy because of its reduced cross section, it relieves the inner sides of the bend points that, without tapers, are the regions where load is greatest. However, the bridge structure as a whole is weakened by the tapers 18.

The maximum stress in the stent generated by a bending moment is dependent on the section modulus of the structural part in the corresponding cross section, with a given external bending moment. The result of this is that a targeted effect on the section modulus of a stent near its node regions can influence the maximum stresses arising. The principle of the taper influences the maximum stress in the surface layer through an actual narrowing of a bridge. A narrowed bridge, however, has a disadvantageous effect when a stent is loaded, because the structure is strongly stressed by the plastic deformation in the tapered region. The deformation energy then concentrates on a relatively small material volume.

Upon alternate flexural loading of a tapered bridge on an expanded stent, caused by the usual contractions in a blood vessel, the tapered area is subjected, not only to a remaining primary stress, but also to an alternating stress. The smaller the primary stress caused by the plastic deformation, the greater the superposed alternating stress can be.

By contrast, the invention optimizes the bridge structure in terms of a reduction in induced stresses and in terms of the attainable strength after a deformation of the bridge structure. The principle according to the invention means that the stresses arising in the deformed areas are not reduced in their entirety but instead are distributed in a targeted way into other structural areas. For this purpose, the section modulus of the deformed structure is influenced in a deliberate manner.

To achieve this variation in section modulus according to the invention, the at least one bridge near the node region is designed along its length with different sizes of cross-sectional areas transverse to the longitudinal axis of the bridge. In this context, the longitudinal axis of the bridge means that axis of the bridge that extends essentially from one node region at one end of the bridge to the node region at the opposite end of the bridge. The associated cross-sectional area can also be designated as a projection of the cross section to the lever arm of the acting bending moment. According to the invention, the projection is varied in such a way that the section modulus is greater some distance away from the insides of curves of the bridge than it is in these curves themselves. In this way, deformation energy is in turn shifted from the region of greatest load to at least partially into the bridge.

Moreover, according to a preferred embodiment, the at least one bridge near the node region is designed along its length with substantially identical cross-sectional areas transverse to its main line. In this context, the main line is that (imaginary) line along which the bridge in question extends. This line is in particular curved when the bridge itself is curved or bent. Since, according to the invention, the cross-sectional area of the bridge transverses this main line, it is always comparatively large. Therefore, weakening caused by tapers, as can occur in the prior art, is substantially avoided.

Particularly, viewed in the jacket surface of the stent, the width of the at least one bridge according to the invention, at least near the node region, is substantially the same size along the length thereof. In this way, compared to a tapered bridge, the volume taken up by plastic deformation energy is greater. In this way, the primary stress remaining after the plastic deformation is smaller, since the same amount of energy is distributed across a greater volume. The alternating load that can be taken up is greater by this amount.

The stated advantages are particularly evident in a stent according to the invention in which the at least one bridge is designed near the node region, with an undulated shape along its length. With this shape, the stresses that arise are deliberately distributed into other areas of the bridge structure, without the stresses in the deformed areas being substantially reduced in their entirety.

The stent according to the present invention is provided overall with a bridge structure in which each individual bridge is designed with an undulated shape along its entire length extending between two node regions. The undulated shape of the at least one bridge can easily be produced by a punching or laser-welding process, by it being formed or cut out in the jacket surface of the stent. To ensure that the desired stress distribution in the case of loading is especially uniform, the undulated shape of the at least one bridge should moreover have alternating curves with substantially identical radii of curvature.

According to the invention, a method for producing a stent is also proposed, with the following steps: forming a bridge structure with at least two bridges and a node region arranged between them for coupling the bridges to one another, and forming at least one of the bridges near the node region in such a way that its section modulus varies along the length of the bridge, and the stresses arising at the node region upon deformation of the stent are distributed in the longitudinal direction of the bridge.

According to a preferred embodiment of the invention, in the formation step, the at least one bridge near the node region is designed along its length with different sizes of cross-sectional areas transverse to the longitudinal axis of the bridge.

Preferably, in the formation step, the at least one bridge near the node region is designed along its length with substantially identical cross-sectional areas transverse to its main line.

Also preferably, in the formation step, viewed in the jacket surface of the stent, the width of the at least one bridge, at least near the node region, is substantially the same size along its length.

Most preferably, in the formation step, the at least one bridge is designed, near the node region, with an undulated shape along its length.

More preferably, in the formation step, the at least one bridge is designed with an undulated shape along its entire length extending between two node regions.

The undulated shape of the at least one bridge is preferably formed in the jacket surface of the stent.

Preferably, the undulated shape of the at least one bridge is designed with alternating curves with in particular substantially identical radii of curvature.

DESCRIPTION OF THE DRAWINGS

Objects and advantages together with the operation of the invention may be better understood by reference to the following detailed description taken in connection with the following illustrations, wherein:

FIG. 3a shows a plan view of a single bridge of the bridge structure according to FIG. 2, illustrating an example angular specification.

DETAILED DESCRIPTION

Figure 1:
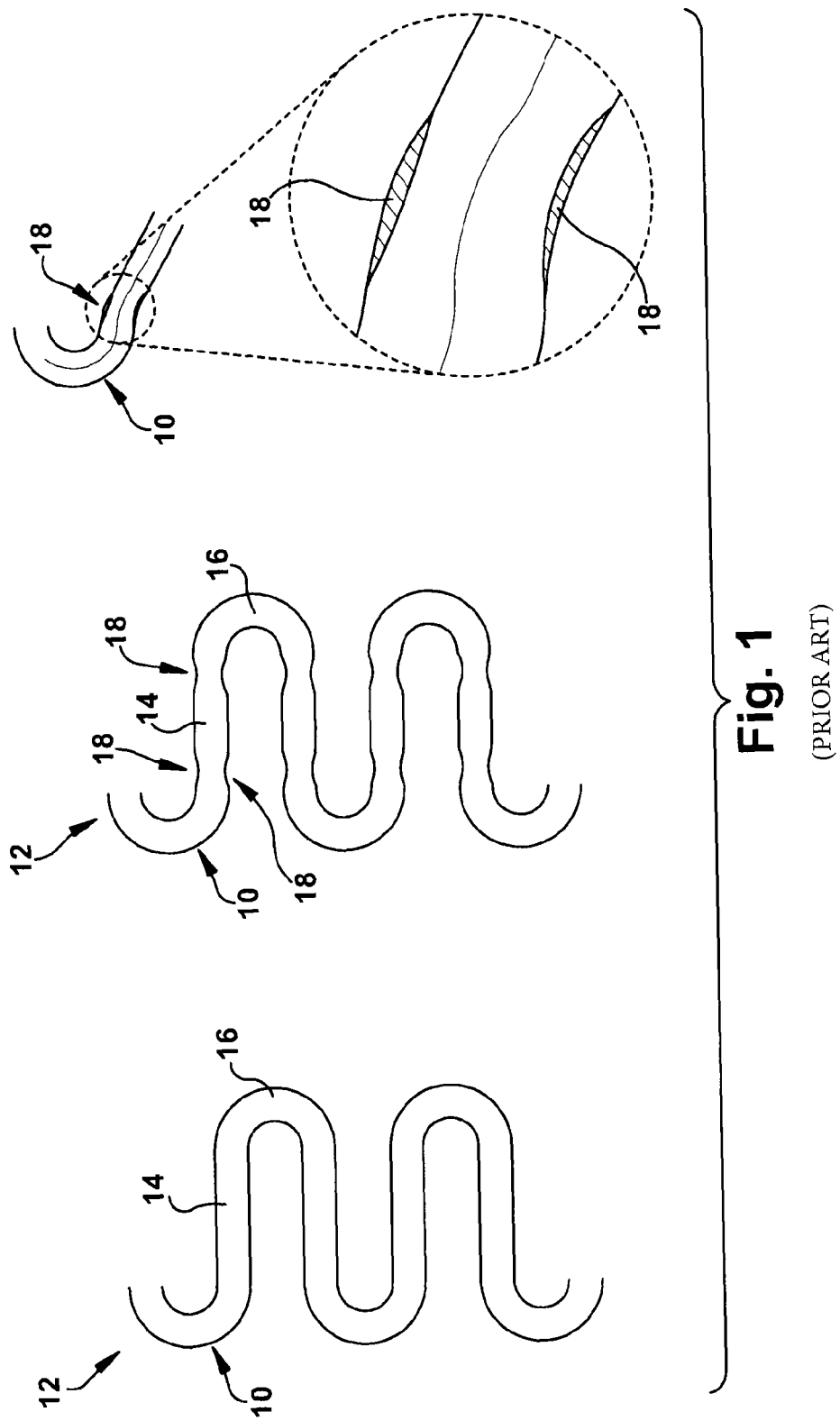
FIG. 1 shows greatly enlarged partial views of bridge structures of known stents.

In contrast to FIG. 1 already discussed above, FIG. 2 shows a stent 20 according to an embodiment of the present invention with a bridge structure 22 in which bridges 24 are coupled to one another at node regions 26.

The bridges 24 are designed with an undulated shape along at least a portion of their length extending between two node regions 26, said undulated shape having been formed from a process such as cutting it out by a laser cutting process from a thin-walled material of a jacket surface of the stent 20. The undulated shape is designed with a number of bulges as a sequence of concave and convex arches or alternating radius elements. In the illustrative embodiment shown, such concave and convex arches are formed in succession on a single bridge 24. There can be between 3 and 12 such concave and convex arches, and in particular between 5 and 10 arches.

The undulated shape of the bridges 24 can be provided in some areas of the stent 20, i.e., not all bridges 24 are provided with an undulated shape and/or the undulated shape is provided only at one area of the individual bridge 24. For example, a bridge 24 may be provided with undulations at a portion near the node region 26 and may have no undulations at a portion further away from the node. Thus, the bridges 24 can provide a distribution of the stresses arising during widening of the stent 20 preferably in those areas that are subjected to the greatest stress during widening of the stent 20.

Alternatively, or in addition, the stent can be produced by a punching method. The stent 20 is in this case can be produced from stainless steel or cobalt/chromium/tantalum alloys. The stent 20 is preferably widened by means of a widening device, for example a balloon catheter, in the body. Materials that can generally be used include tantalum, niobium or cobalt alloys.

However, it is also conceivable to have stents made from other materials, for example polymers, self-degradable materials (e.g., lactic acid materials or derivatives), and stents made of other self-expandable materials or (preferably temperature-dependent) shape-memory materials.

Figure 3:
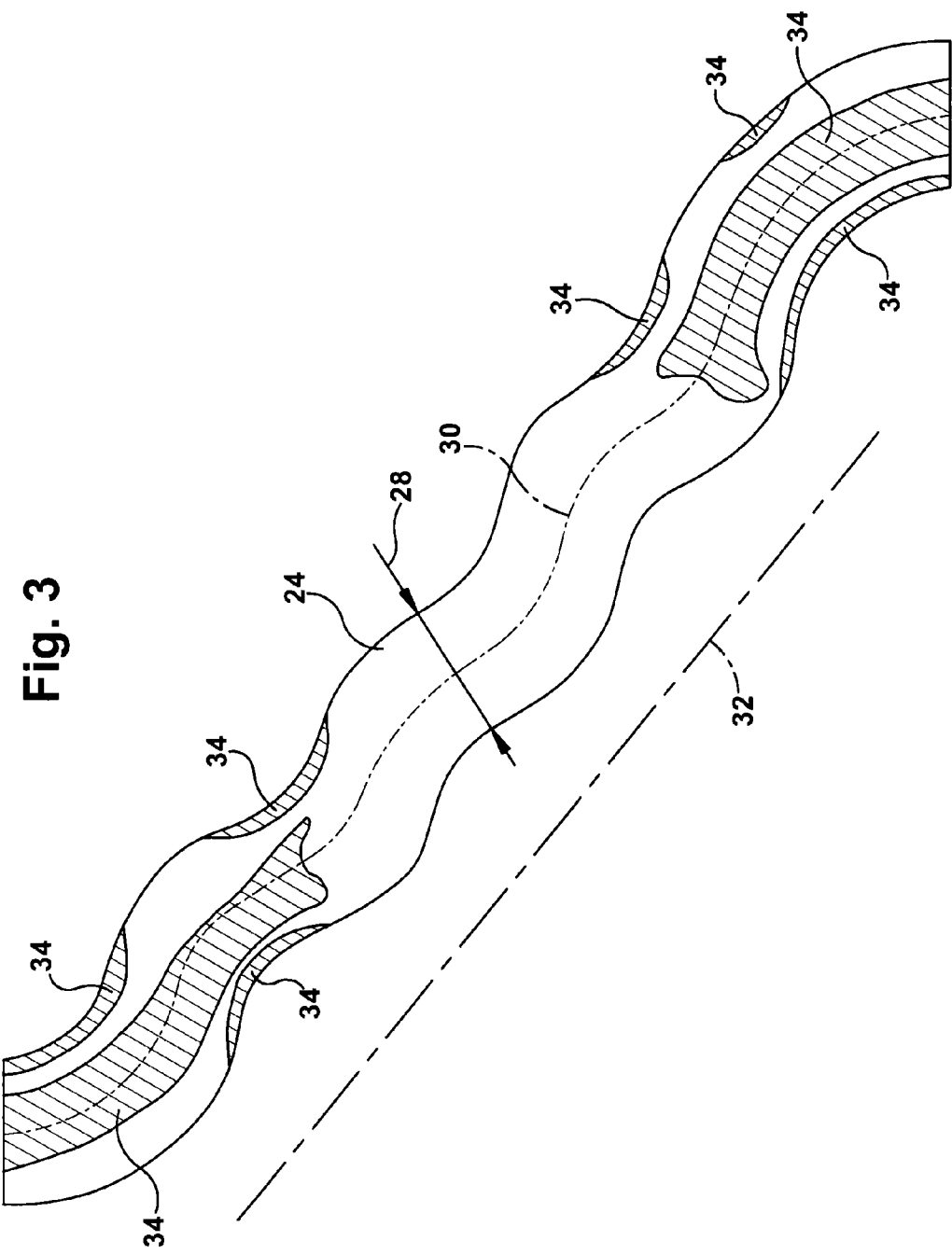
FIG. 3 shows an enlarged plan view of a single bridge of the bridge structure according to FIG. 2, with simulated stress regions.

As can be seen in particular from FIG. 3, viewed in the jacket surface of the stent 20, the width 28 of each bridge 24 is substantially the same size along the length thereof. Moreover, because the thickness of the material of the jacket surface of the stent 20 is also substantially the same overall, each bridge 24 is designed along its length with substantially identical cross-sectional areas transverse to its main line 30. Viewed along the length of the bridge 24, by contrast the cross-sectional areas transverse to the longitudinal axis 32 of the bridge 24 are of different sizes.

In this way, on each bridge 24, in particular near the associated node region 26, the section moduli of the bridge 24 are varied along the length thereof, and the stresses arising at the node region 26 upon deformation of the stent 20 are distributed in the longitudinal direction of the bridge at least in some parts or some areas. Although stresses near the node region 26 are thus not reduced in their entirety, they are however distributed in a targeted manner into other structural areas of the bridge structure 22, as can be seen from the areas of increased stress 34 shown in a simplified manner in FIG. 3.

Figure 2:
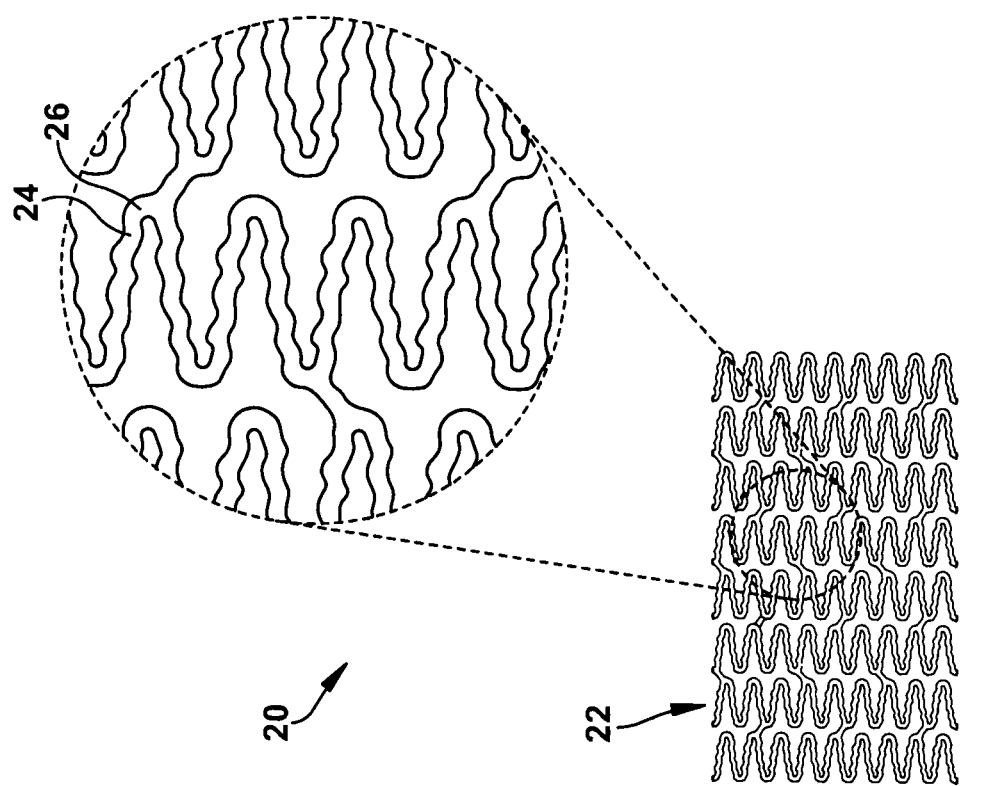
FIG. 2 shows an enlarged plan view with an enlarged detail of the bridge structure of a stent according to an embodiment of the present invention.

In an embodiment, the stent 20 may include both macro and micro undulations. For example, as illustrated in FIG. 2, the bridges 24 may be arranged in a generally sinusoidal share or S-shape, having both curved and straight portions, as is known in the art. The undulations may extend along curved and straight portion of the sinusoidal shaped bridges 24.

The undulations as described herein may be smaller in scale than the overall sinusoidal shape of the bridges. For example, the undulations may include concave and convex arches each having an apex 36. The arches may be sized and shaped such that the length between successive concave arches is in the range of approximately 0.05 millimeters to approximately 0.4 millimeters.

The arches may configured to a specified angle of undulation. For example, the angle 38 of the arches may be in the range of approximately 3 degrees to approximately 30 degrees along the length of the arch. As used herein, the arch angle may be defined as the angle between a first line 40 orthogonal or perpendicular to the outer surface of the bridge 24 at a point along the bridge and a second line 42 orthogonal to the outer surface of the bridge 24 at the apex 36 of the next arch.

The stent 20 according to the invention or a preferred embodiment thereof can be produced both from tubular material and also from flat material. In the latter case the stent subsequently being rolled up, welded and/or finished. The stent 20 can also be produced by means of laser cutting, laser removal, photochemical etching and/or erosion. The stent 20 can also be produced with the stent structure being made in an at least partially expanded form, and the stent then being reduced in size to a compressed shape for insertion into the catheter, for example, before then being at least partially expanded again in the body.

Embodiments of the present invention have been described above and, obviously, modifications and alternations will occur to others upon a reading and understanding of this specification. In addition, the method of production described above is not limited to the order in which the steps above are recited. The claims as follows are intended to include all modifications and alterations insofar as they come within the scope of the claims or the equivalents thereof.

The invention claimed is:

1. A stent for implantation into a living body comprising:
a first bridge extending around a circumference of said stent and having a length along a longitudinal axis;
a second bridge extending around the circumference of said stent and having a length along a longitudinal axis;
a node region coupling said first bridge to said second bridge;
wherein said first bridge includes an undulating portion comprising a plurality of arches each having an apex, and wherein the length between the apex of consecutive arches is between 0.05 millimeters and 0.4 millimeters;
wherein said plurality of arches have a maximum arch angle between approximately 3 degrees and approximately 30 degrees, and wherein said arch angle is the angle between a first line perpendicular to an outer surface of said first bridge at a point along the length of the first bridge and a second line perpendicular to the outer surface of the first bridge at said apex of said arch; and
wherein the width of said first bridge is constant along its length.

2. The stent of claim 1, wherein the undulating portion of said first bridge extends along its entire length.

3. The stent of claim 2, wherein the undulating portion of said first bridge is formed in a jacket surface of the stent.

4. The stent of claim 1, wherein upon deformation of the stent, stresses arising at said node region are distributed in a longitudinal direction of said bridges in a targeted way.

5. The stent of claim 1, wherein said plurality of arches have approximately identical radii of curvature.

6. The stent of claim 1, wherein at least a portion of said first bridge is arranged in a sinusoidal shape.

7. The stent of claim 6, wherein said undulating portion extends along a length of said sinusoidal shaped first bridge.

* * * * *